US00PP23127P3

(12) United States Plant Patent
Leis et al.

(10) Patent No.: US PP23,127 P3
(45) Date of Patent: Oct. 23, 2012

(54) STRAWBERRY PLANT NAMED 'DELY'

(50) Latin Name: ***Fragaria ananassa* Duch**
Varietal Denomination: DELY

(75) Inventors: Michelangelo Leis, Ferrara (IT); Alessio Martinelli, Ferrara (IT); Gianfranco Castagnoli, Quingentole (IT); Donata Azzolini, legal representative, Quingentole (IT); Pietro Castagnoli, legal representative, Quingentole (IT); Alessandro Castagnoli, legal representative, Quingentole (IT)

(73) Assignee: C.I.V. Consorzio Italiano Vivaisti—Societa Consortile A R.L., Ferrara (IT)

( * ) Notice: Subject to any disclaimer, the term of this patent is extended or adjusted under 35 U.S.C. 154(b) by 0 days.

(21) Appl. No.: 13/067,082

(22) Filed: May 6, 2011

(65) Prior Publication Data

US 2012/0210475 P1 Aug. 16, 2012

(30) Foreign Application Priority Data

Feb. 14, 2011 (QZ) ..... PBR 20110363

(51) Int. Cl.
*A01H 5/00* (2006.01)

(52) U.S. Cl. ..... Plt./208

(58) Field of Classification Search ..... Plt./208
See application file for complete search history.

*Primary Examiner* — Annette Para
(74) *Attorney, Agent, or Firm* — Foley & Lardner LLP

(57) ABSTRACT

A new and distinct variety of *Fragaria ananassa Duch* named 'DELY', characterized by the description herein.

4 Drawing Sheets

Latin name of the genus and species claimed: *Fragaria ananassa Duch.*

Variety denomination: 'DELY'.

BACKGROUND OF THE INVENTION

The present invention relates to a new and distinct strawberry variety named 'DELY', which was the result of a controlled cross between not released selections of Consorzio Italiano Vivaisti T2-6xA20-17

The progeny was first asexually propagated by stolons in S. Giuseppe di Comacchio Ferrara Italy in 2004.

The Dely variety was tested over the next several years in different European areas with continental climates. The test started in 2005 till 2010.

BRIEF SUMMARY OF THE INVENTION

Plants of the new Strawberry variety 'DELY' (not patented) can be distinguished from plants of the Strawberry variety 'CLERY' by the following unique combination of characteristics described in Table 1:

TABLE 1

| Comparison with Comparison Variety | | | |
|---|---|---|---|
| Denomination of similar variety | Characteristic in which the similar variety is different | State of expression of similar variety | State of expression of candidate variety |
| 'CLERY' | Firmness<br>Vigour | Very firm<br>medium | Medium-firm<br>strong |

Asexual reproduction of this new variety by stolons shows that the foregoing and all other characteristics and distinctions come true to form and are established and transmitted through succeeding propagations. The new cultivar reproduces true to type.

BRIEF DESCRIPTION OF THE PHOTOGRAPHS

The accompanying photographs illustrate the overall appearance of the new Strawberry 'DELY' showing the colors as true as is reasonably possible with colored reproductions of this type. Colors in the photographs may differ slightly from the color value cited in the detailed botanical description, which accurately describe the color of 'DELY'.

Figure 1:
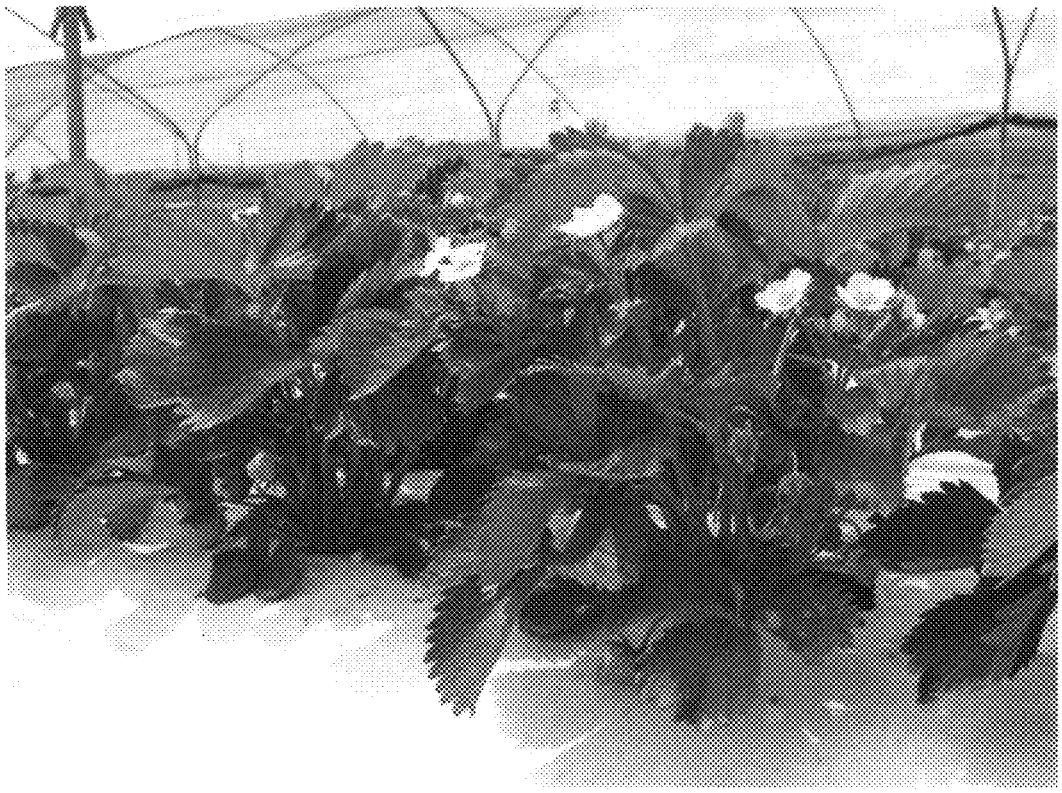
Figure 2:
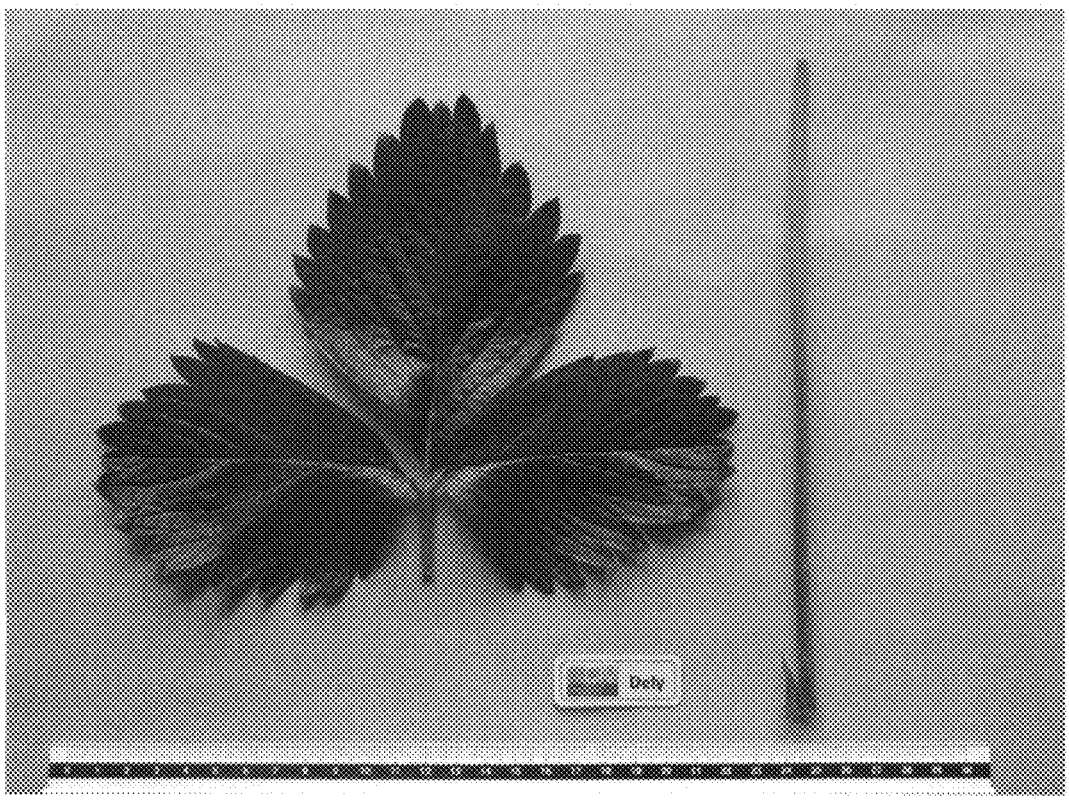
Figure 3:
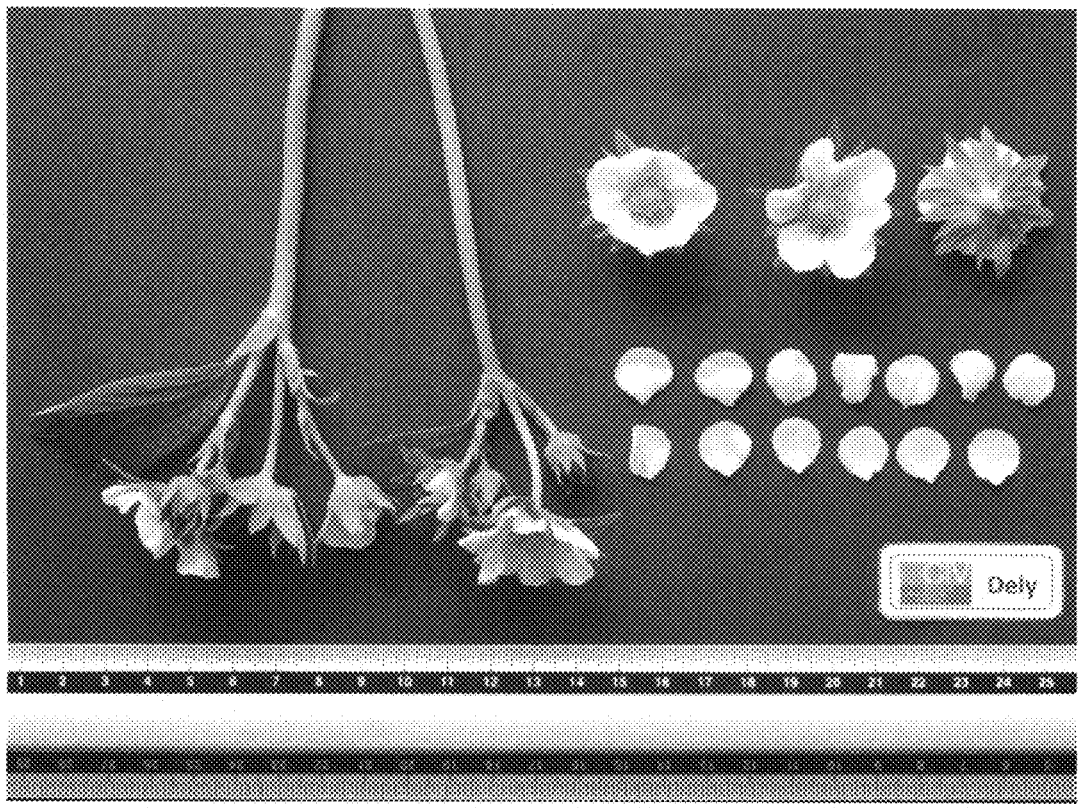
Figure 4:
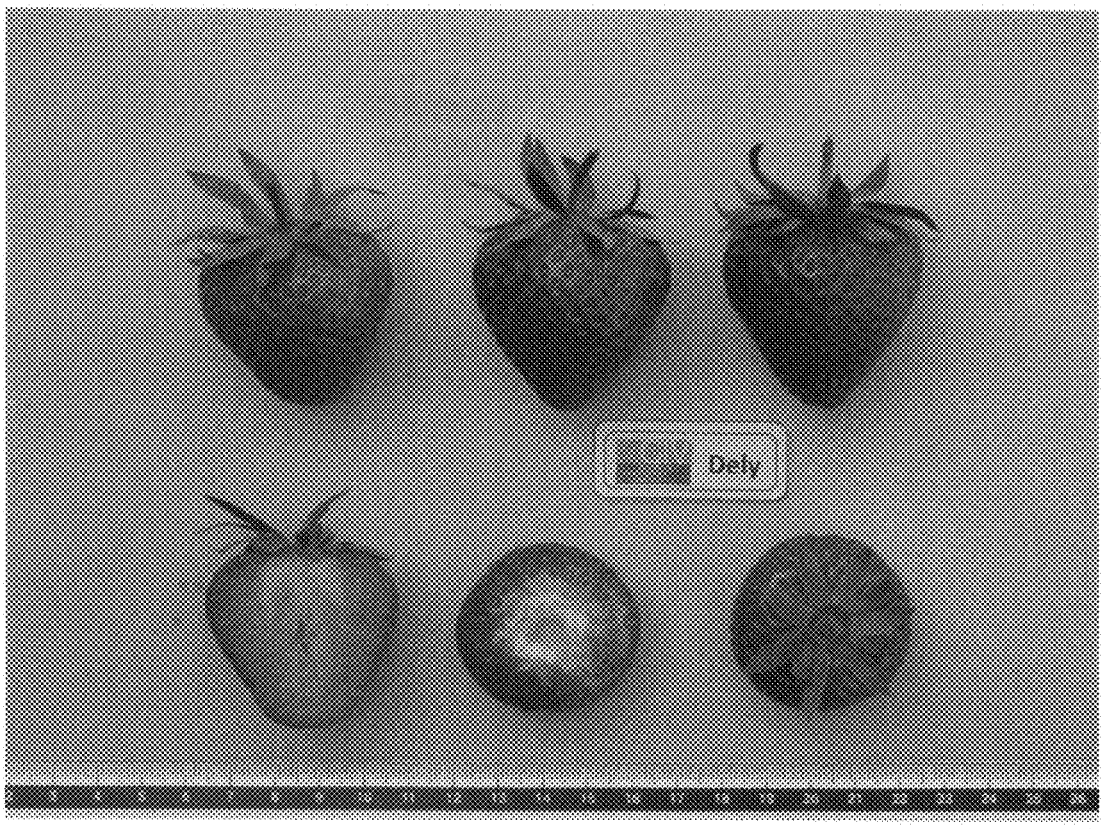

FIG. 1 shows the plant of 'DELY';
FIG. 2 shows the leaves of 'DELY';
FIG. 3 shows the flowers of 'DELY' and
FIG. 4 shows the fruits of 'DELY'.

The colors of this illustration may vary with lighting conditions and, therefore, color characteristics of this new variety should be determined with reference to the observations described herein, rather than from these illustrations alone.

DETAILED BOTANICAL DESCRIPTION

The following detailed description of the Dely variety, unless otherwise noted, is based on observations taken of plants and fruits, and asexually reproduced progeny, grown at S. Giuseppe di Comacchio Ferrara Italy.

The observed plants were one year old plants, produced in the nursery in Ferrara in 2009, then stored in cold storage at −1° C. from December 2009 and planted in the production field c/o CIV on 30 Jul. 2010.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. Color designations are made with reference to The Royal Horticultural Society (R.H.S.) Colour Chart.

PLANT:

*Habit*.—Semi-upright.

*Density*.—Medium.

*Vigor*.—Strong.

*Overall shape*.—Globose.

*Height*.—About 0.34 meters.

*Width*.—About 0.46 meters.

Leaf:

*Upperside*.—RHS 141A green group; underside: RHS 138B green group.

*Length*.—0.15 m.

*Width*.—0.20 m.

*Cross section*.—Concave.

*Leaf surface undulation or blistering*.—Medium.

*Number of leaflets*.—Three only.

*Leaf stem characteristics*.—Color RHS 145 A, green group. Position of hairs: slightly outwards. Length: About 19 cm.

*Terminal leaflet*.—Length/width ratio: 1.1, moderately longer. Length: About 11 cm. Width: About 10 cm. Shape of base: acute. Shape of teeth: Crenate.

*Petiole*.—Position of hairs: slightly outwards. Length: About 19 cm.

*Stipule*.—Anthocyanin coloration: weak. Color RHS 46 A red group.

*Stolons*.—Number: about 10-15. Thickness: Medium, about 2.5 mm. Pubescence: sparse. Color RHS 145 A, yellow green group.

Inflorescence: Position relative to foliage is at same level.

*Length*.—About 22 cm.

*Flower*.—Size. Medium. Size of calyx relative to corolla. Same size. Spacing of petals. Overlapping.

*Flower characteristics*.—Diameter primary flowers. About 3.6 cm. Diameter secondary flowers. About 3.0 cm. Number of petals. Normally 6-7. Color — RHS white group (near 155 B). Fragrance: No significant fragrance. Time from bloom to mature fruit. — About 22 to 28 days.

Reproductive organs:

*Stamens*.—Numerous with pollen present, fertile and abundant. Length approximately 3 mm.

*Anthers*.—Generally average in size (length about 1.5 mm, width about 1 mm). Color — RHS yellow group (near 12 B) and darkening color RHS 12 A with advanced maturity. Pollen. — Fertile and abundant. Color — RHS yellow orange group (near 14 B). Pistils. — Numerous, generally average in size. Color — RHS yellow group (near 13 B).

*Petal*.—Length/width ratio: 1,05.

*Fruit truss*.—Attitude: Semi-erect.

Fruit:

*Fruit*.—Ratio of length/maximum width: equal or moderately longer.

*Color of mature fruit*.—RHS 45 A red group.

*Color of internal fruit*.—RHS 44 A red group, RHS 39 A orange-red group, and RHS 155 D white group.

*Length*.—Average 43.8 mm.

*Width*.—Average 42.8 mm.

*Calyx diameter*.—Average 49 mm.

*Average weight*.—About 19 to 31 grams.

*Achene color*.—RHS 152 C yellow green group.

*Number of achenes per berry*.—300-360.

*Achene size*.—Length about 1.2 mm, width about 1 mm.

*Weight of* 1000 *achenes*.—About 0.68 grams.

*Peduncle length of inflorescence stem*.—Primary fruit about 6 to 9 cm. Secondary fruit about 6 cm. Color: near RHS 145 A, yellow green group.

*Marketable yield* (*gm/plant*).—About 600 grams.

*Fruit size*.—Medium to large.

*Predominant shape*.—Conical.

*Difference in shapes between primary and secondary fruit*.—Moderate. Band without achenes: absent or very narrow.

*Unevenness of surface*.—Even or very slightly uneven.

*Evenness of color*.—Even or very slightly uneven.

*Glossiness*.—Strong.

*Insertion of achenes*.—Level with surface.

*Insertion of calyx*.—Level with surface.

*Attitude of the calyx*.—Outwards.

*Size of calyx in relation to fruit diameter*.—Same size.

*Adherence of calyx*.—Medium.

*Firmness of flesh*.—Medium-firm.

*Hollow center expression*.—Medium.

*Flavor*.—Very good.

*Soluble solids* (% *brix*).—About 9.

*Time of first flowering*.—Early, from one week of April in S. Giuseppe di Comacchio Ferrara Italy.

*Time of first harvesting*.—Early, from last week of April in S. Giuseppe di Comacchio Ferrara Italy.

*Harvest period*.—About one month from last week of April to last week of May in S. Giuseppe di Comacchio Ferrara Italy.

*Type of bearing*.—Not remontant.

Disease resistance: The 'DELY' variety as been tested for several years and it has manifested a good rusticity plant, quite resistant to leaf and root diseases.

What is claimed is:

1. A new and distinct variety of *Fragaria ananassa Duch* plant named 'DELY', as illustrated and described herein.

* * * * *